(12) United States Patent
Lin et al.

(10) Patent No.: US 9,500,592 B2
(45) Date of Patent: Nov. 22, 2016

(54) SURFACE-ENHANCED RAMAN SCATTERING SUBSTRATE

(71) Applicant: INDUSTRIAL TECHNOLOGY RESEARCH INSTITUTE, Hsinchu (TW)

(72) Inventors: Ding-Zheng Lin, Taipei (TW); Tsung-Dar Cheng, Taipei (TW); Hsiao-Feng Huang, Taoyuan (TW); Ping-Chen Chen, Taipei (TW)

(73) Assignee: INDUSTRIAL TECHNOLOGY RESEARCH INSTITUTE (TW)

( * ) Notice: Subject to any disclaimer, the term of this patent is extended or adjusted under 35 U.S.C. 154(b) by 183 days.

(21) Appl. No.: 14/164,742

(22) Filed: Jan. 27, 2014

(65) Prior Publication Data

US 2014/0362373 A1    Dec. 11, 2014

(30) Foreign Application Priority Data

Jun. 5, 2013  (TW) ............................. 102119879 A

(51) Int. Cl.
*G01N 21/65* (2006.01)

(52) U.S. Cl.
CPC ................... *G01N 21/658* (2013.01)

(58) Field of Classification Search
CPC .................................................. G01N 21/658
See application file for complete search history.

(56) References Cited

U.S. PATENT DOCUMENTS

| 7,929,133 | B2 | 4/2011 | Wang et al. |
| 8,003,408 | B2 | 8/2011 | Zhang et al. |
| 8,314,932 | B2 | 11/2012 | Ou et al. |
| 2003/0207090 | A1* | 11/2003 | Arora ............. B41M 3/14  428/195.1 |
| 2006/0034729 | A1* | 2/2006 | Poponin ........... G01N 21/658  422/82.05 |
| 2009/0317608 | A1* | 12/2009 | Furukawa ........ G03F 7/0757  428/195.1 |
| 2010/0129623 | A1 | 5/2010 | Johansson et al. |
| 2010/0284001 | A1 | 11/2010 | Moskovits et al. |
| 2012/0287427 | A1* | 11/2012 | Li ...................... B82Y 15/00  356/301 |
| 2013/0196122 | A1* | 8/2013 | Park .................. G03F 7/0002  428/195.1 |
| 2015/0065390 | A1* | 3/2015 | Bratkovski ........ B01L 3/5088  506/12 |
| 2016/0245772 | A1* | 8/2016 | Anderson ............. H01B 1/04 |

FOREIGN PATENT DOCUMENTS

| CN | 1957245 | 5/2007 |
| CN | 102078787 | 6/2011 |
| CN | 102608103 | 7/2012 |
| CN | 103103494 | 5/2013 |
| JP | 2005-77362 | 3/2005 |

(Continued)

OTHER PUBLICATIONS

Office Action (and Prior Art reference Index) dated Sep. 2, 2014 from corresponding No. TW 102119879.

(Continued)

*Primary Examiner* — Kara E Geisel
*Assistant Examiner* — Shawn Decenzo
(74) *Attorney, Agent, or Firm* — Hauptman Ham, LLP

(57) ABSTRACT

The disclosure provides a surface-enhanced Raman scattering substrate, including: a surface-enhanced Raman scattering (SERS)-active substrate; a patterned hydrophilic region and a patterned hydrophobic region formed on the SERS-active substrate, wherein a water contact angle difference between the patterned hydrophilic region and the patterned hydrophobic region is in a range from about 29 degrees to about 90 degrees.

18 Claims, 6 Drawing Sheets

(56) References Cited

FOREIGN PATENT DOCUMENTS

| JP | 2009-31023 | 2/2009 |
|---|---|---|
| TW | 200823447 | 6/2008 |
| TW | I360657 | 3/2012 |
| TW | 201221941 | 6/2012 |
| TW | 201250231 | 12/2012 |
| TW | 201250631 | 12/2012 |
| TW | 201307828 | 2/2013 |
| WO | 2007094817 | 8/2007 |

OTHER PUBLICATIONS

James, N. et al., "Combinatorial chemistry methods for coating development V: generating a combinatorial array of uniform coating samples", Elsevier, Progress in Organic Coatings, 2003, pp. 128-135.

Peter J. et al., "Suppression of the coffee-ring effect by shape-dependent capillary interactions", Nature, 2011, vol. 476, pp. 308-311.

Thiruvelu Bhuvana et al., "A SERS-Active nanocrystalline Pd Substrate and its Nanopatterning Leading to Biochip Fabrication", small, 2008, vol. 4, No. 5, pp. 670-676.

Deborah Lau et al., "Fabrication of nanoparticle micro-arrays patterned using direct write laser photoreduction", Applied Surface Science, vol. 255, Issue 5, pp. 2159-2161.

Hyeon Suk et al., Direct patterning of silver colloids by microcontact printing: possibility as SERS substrate array, Vibrational Spectroscopy, 2002, p. 79-82.

Robert D. Deegan et al., "Capillary flow as the cause of ring stains from dried liquid drops", Nature 389, pp. 827-829 (1997).

Juhui Ko, et al., "SERS-based immunoassay of tumor marker VEGF using DNA aptamers and silica-encapsulated hollow gold nanospheres", Phys. Chem. Chem. Phys., 2013, 15, pp. 5379-5385; www.rsc.org/pccp, DOI: 10.1039/c2cp43155f.

Yongxia Huang, et al., "SERS study of Ag nanoparticles electrodeposited on patterned $TiO_2$ nanotube films", Journal of Raman Spectroscopy, 2011, 42, pp. 986-991; Published online in Wiley Online Library: Nov. 23, 2010 (wileyonlinelibrary.com) DOI 10.1002/jrs2830.

Office Action dated Apr. 20, 2016 from corresponding No. CN 201310283627.8.

* cited by examiner

US 9,500,592 B2

SURFACE-ENHANCED RAMAN SCATTERING SUBSTRATE

CROSS REFERENCE TO RELATED APPLICATIONS

This Application claims priority of Taiwan Patent Application No. 102119879, filed on Jun. 5, 2013, the entirety of which is incorporated by reference herein.

TECHNICAL FIELD

The present disclosure relates to a substrate, and in particular relates to a surface-enhanced Raman scattering (SERS) substrate.

BACKGROUND

There are several poisonous chemical pollutants in the environment, and these pollutants have different maximum allowable concentrations, e.g. benzene (5.1 ppb), Pb (50 ppb), Cd (5 ppb), paraquat (20 ppb), 1,1,1-trichloroethane (0.2 ppm). However, traditional detection instruments are expensive and take a lot of time for measurements, thereby limiting their time-effectiveness and popularity. Therefore, those skilled in the art are devoted to developing a highly sensitive, rapid, and low cost trace-detection device to analyze biological and chemical analytes.

A Raman Scattering Spectrum has the advantages of fingerprint specificity and multi-domain applications, and thus it is applied in trace detection. However, the Raman scattering intensity is very weak. Scientists use a metal structure to induce the surface-Enhanced Raman Scattering (SERS) to amplify the scattering intensity $10^4$-$10^{12}$ times.

However, when the analyte is put on the surface-enhanced Raman scattering substrate and then is dried, the reproducibility of the Raman scattering signal is bad due to the non-uniform distribution of the analyte. Therefore, the limit of detection (LOD) is quite limited.

Accordingly, there is a need to develop a SERS substrate. That will improve the reproducibility of the Raman scattering signal.

SUMMARY

The disclosure provides a surface-enhanced Raman scattering substrate, including: surface enhanced Raman scattering (SERS)-active substrate; a patterned hydrophilic region and a patterned hydrophobic region formed on the SERS-active substrate, wherein a water contact angle difference between the patterned hydrophilic region and the patterned hydrophobic region is in a range from about 29 degrees to about 90 degrees.

A detailed description is given in the following embodiments with reference to the accompanying drawings.

BRIEF DESCRIPTION OF THE DRAWINGS

For a more complete understanding of the present disclosure, and the advantages thereof, reference is now made to the following descriptions taken in conjunction with the accompanying drawings, in which.

DETAILED DESCRIPTION

Figure 1B:
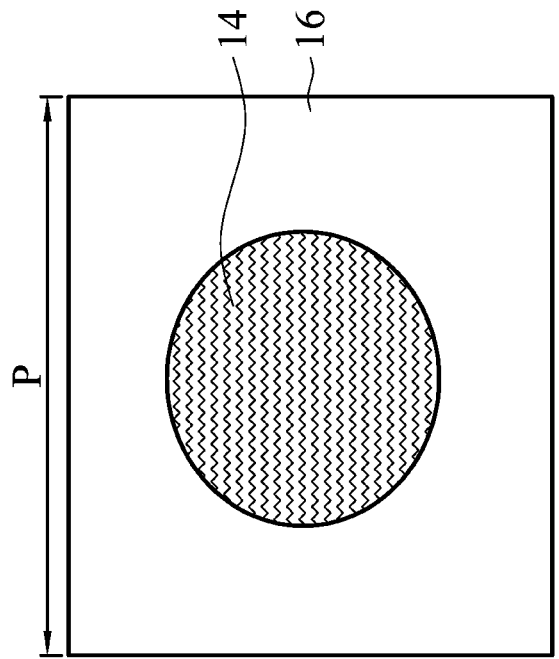
FIG. 1B shows a top-view schematic representation of FIG. 1A in accordance with a first embodiment of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

FIG. 1 shows a cross-sectional schematic representation of a surface-enhanced Raman scattering (SERS) substrate 10 of a first embodiment of the disclosure. The surface-enhanced enhanced Raman scattering (SERS) substrate 10 comprises a patterned hydrophilic region 14 and a patterned hydrophobic region 16 both formed on a SERS-active substrate 12. It should be noted that the SERS-active substrate 12 is a continuous SERS-active substrate, and overall surfaces of the SERS-active substrate 12 are contributed to enhance Raman scattering.

Referring to FIG. 1, the patterned hydrophilic region 14 is a hydrophilic layer, and the patterned hydrophobic region 16 is the SERS-active substrate 12 with a hydrophobic surface. When an analyte (not shown) is disposed on the hydrophilic layer, the hydrophilic layer has a thickness T1 in a range from about 0.01 nm to about 10 nm. Note that the Raman scattering signal is affected by the distance from the analyte to the hot spot on SERS active material. If the thickness of the hydrophilic layer is larger than about 10 nm, the Raman scattering signal is too weak to be observed.

The patterned hydrophilic region 14 is made of a material comprising an organic material or inorganic material. The organic material comprises polysiloxane, tetraethoxysilane (TEOS), tetramethoxysilane, hexamethyldisiloxane (HMDS), HMDS, aluminum butoxide, diethylzinc, triethylaluminum, trimethylaluminum, metal alkyls, titanium tetraisopropoxide, titanium tetrapropoxide, metal alkoxides, zinc nitrate, aluminum nitrate, metal nitride, zinc acetate, aluminum acetate, tin acetate, metal acetate, zinc sulfate, aluminum sulfate, stannous sulfate, metal sulfate, zinc chloride, zirconium tetrachloride, aluminum chloride, titanium chloride, metal chloride, metal chloride liquid, metal chloride steam or vapor, or combinations thereof. The inorganic material comprises silicon oxide ($SiO_2$), metal, metal oxide or combinations thereof. The metal comprises silver (Ag), gold (Au), zinc (Zn), zirconium (Zr), tin (Sn), titanium (Ti), barium (Ba), platinum (Pt), aluminum (Al) or combinations thereof.

In one preferred embodiment, the hydrophilic layer is formed by using a plasma-assisted deposition process. During the plasma-assisted deposition process, a precursor is used. The precursor comprises polysiloxane, tetraethoxysilane (TEOS), tetramethoxysilane, hexamethyldisiloxane (HMDSO), HMDS, aluminum butoxide, diethylzinc, triethylaluminum, trimethylaluminum, metal alkyls, titanium tetraisopropoxide, titanium tetrapropoxide, metal alkoxides, metal nitrate, metal acetate, metal sulphate, metal chloride or combinations thereof.

In one embodiment, a water contact angle difference between the patterned hydrophilic region 14 and the patterned hydrophobic region 16 is in a range from about 90 degrees. In some other embodiments, a water contact angle difference between the patterned hydrophilic region 14 and the patterned hydrophobic region 16 is in a range from about 29 degrees to about 90 degrees.

It should be noted that the patterned hydrophilic region 14 and the patterned hydrophobic region 16 are formed by changing the surface properties of the SERS-active substrate 12. Therefore, the water contact angle difference between different regions is produced. In addition, when the analyte is dried, the analyte is uniformly distributed on the patterned hydrophilic region 14 and the patterned hydrophobic region 16. Therefore, the analyte is concentrated and the reproducibility of the Raman scattering signal is further improved.

Furthermore, in one embodiment, a ratio of an area of the patterned hydrophobic region 16 to an area of the patterned hydrophilic region 14 is in a range from 0.1 to 0.9. In some other embodiments, a ratio of an area of the patterned hydrophobic region 16 to an area of the patterned hydrophilic region 14 is in a range from 0.4 to 0.7.

Figure 1A:
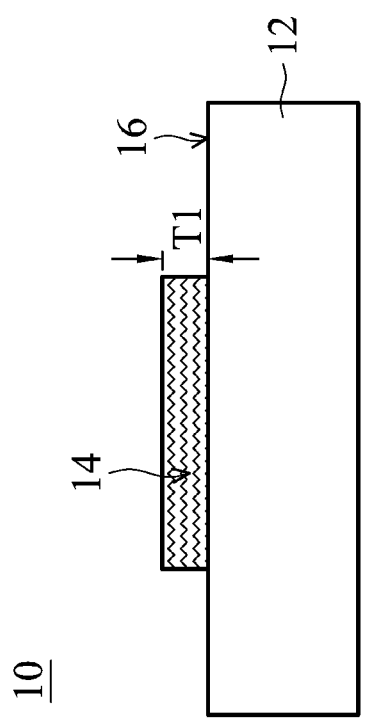
FIG. 1A shows a cross-sectional schematic representation of a surface-enhanced Raman scattering (SERS) substrate in accordance with a first embodiment of the disclosure.

FIG. 1B shows a top-view schematic representation of FIG. 1A in accordance with a second embodiment of the disclosure. As shown in FIG. 1B, the patterned hydrophilic region 14 has a circular shape. However, the hydrophilic region 14 is not limited to having a circular shape, the patterned hydrophilic region 14 may have a regular or irregular shape, the regular shape comprising a rectangular or triangle shape.

Referring to FIG. 1B again, a structure unit is constructed by the patterned hydrophilic region 14 and the patterned hydrophobic region 16. The structure unit has a unit length P in a range from 0.05 μm to 500 μm. The "structure unit" refers to a distribution range of the dried analyte. The distribution range is smaller than or equal to the focusing spot of laser. The focusing spot of Raman spectrometer instruments is generally smaller than about 500 μm.

Figure 2B:
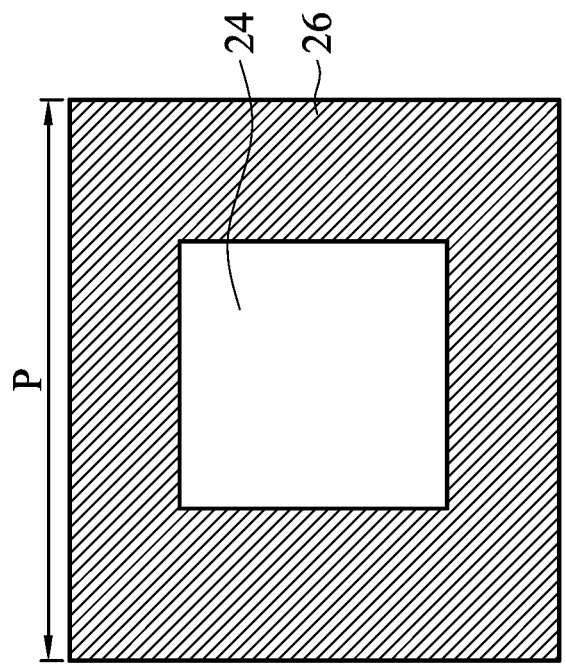
FIG. 2B shows a top-view schematic representation of FIG. 2A in accordance with a second embodiment of the disclosure.
Figure 2A:
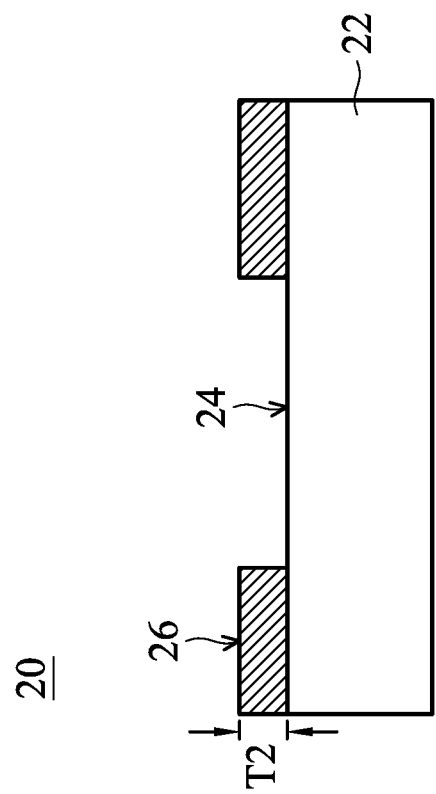
FIG. 2A shows a cross-sectional schematic representation of a surface-enhanced Raman scattering (SERS) substrate in accordance with a second embodiment of the disclosure.

FIG. 2A shows a cross-sectional schematic representation of a surface-enhanced Raman scattering (SERS) substrate in accordance with a second embodiment of the disclosure. The SERS substrate 20 comprises a SERS-active substrate 22, a patterned hydrophilic region 24 and a patterned hydrophobic region 26 formed on the SERS-active substrate 22.

As shown in FIG. 2A, the patterned hydrophobic region 26 is a hydrophobic layer, and the patterned hydrophilic region 24 is a SERS-active substrate 22 with a hydrophilic surface. The patterned hydrophobic region 26 is made of a material comprising polytetrafluoroethene, 1H,1H,2H,2H-Perfluorooctyltrichlorosilane or combinations thereof.

It should be noted that a Raman scattering signal of the analyte is affected by a thickness of a region directly underlying the analyte. Therefore, as shown in FIG. 2A, when the analyte (not shown) is disposed on the hydrophilic surface of SERS substrate, the thickness of the patterned hydrophobic region 26 is not limited to being smaller than 10 nm. In contrast, when the analyte is disposed on the hydrophobic layer, the thickness T2 of the patterned hydrophobic region 26 is in a range from about 0.01 nm to about 10 nm.

FIG. 2B shows a top-view schematic representation of FIG. 2A in accordance with a second embodiment of the disclosure. As shown in FIG. 2B, the patterned hydrophilic region 24 has a rectangular shape. However, the patterned hydrophilic region 24 is not limited to the rectangular shape, the patterned hydrophilic region 24 may have a regular or irregular shape, the regular shape comprising a circular or triangle shape.

Referring to FIG. 2B again, a structure unit is constructed by the patterned hydrophilic region 24 and the patterned hydrophobic region 26. The structure unit has a unit length P in a range from 0.05 μm to 500 μm.

Figure 3B:
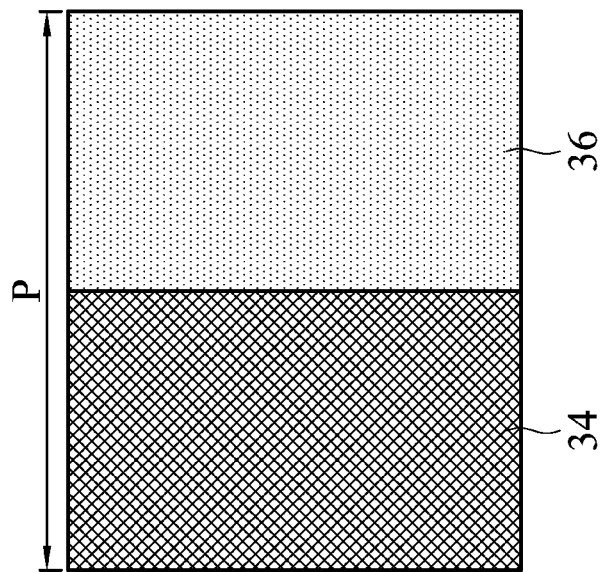
FIG. 3B shows a top-view schematic representation of FIG. 3A in accordance with a third embodiment of the disclosure.
Figure 3A:
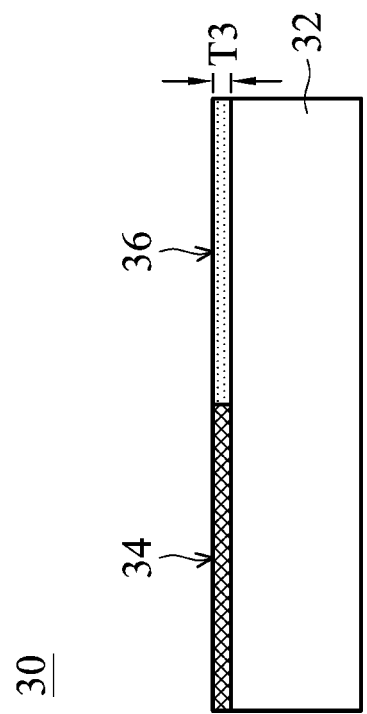
FIG. 3A shows a cross-sectional schematic representation of a surface-Enhanced Raman scattering (SERS) substrate in accordance with a third embodiment of the disclosure.

FIG. 3A shows a cross-sectional schematic representation of a surface-enhanced Raman scattering (SERS) substrate in accordance with a third embodiment of the disclosure. The SERS substrate 30 comprises a SERS-active substrate 32, a patterned hydrophilic region 34 and a patterned hydrophobic region 36 formed on the SERS-active substrate 32.

As shown in FIG. 3A, the patterned hydrophilic region 34 is a hydrophilic layer, and the patterned hydrophobic region 36 is a hydrophobic layer. The material of the hydrophilic layer is the same as the first embodiments, and the material of the hydrophobic layer is the same as the second embodiment, and therefore is omitted herein.

It should be noted that a Raman scattering signal of the analyte is affected by a thickness of a region directly underlying the analyte. Therefore, as shown in FIG. 3A, when the analyte (not shown) is disposed on the hydrophilic surface of the SERS substrate, the thickness T3 of patterned hydrophilic region 34 is in a range from about 0.01 nm to about 10 nm. In contrast, when the analyte is disposed on the hydrophobic layer, the thickness T3 of the patterned hydrophobic region 36 is in a range from about 0.01 nm to about 10 nm.

FIG. 3B shows a top-view schematic representation of FIG. 3A in accordance with a second embodiment of the disclosure. As shown in FIG. 3B, the patterned hydrophilic region 34 has a rectangular shape, and the patterned hydrophobic region has a rectangular shape. However, the shape is not limited to the rectangular shape; a regular or irregular shape is also included in the disclosure, and the regular shape comprises a circular or triangle shape.

Figure 4A:
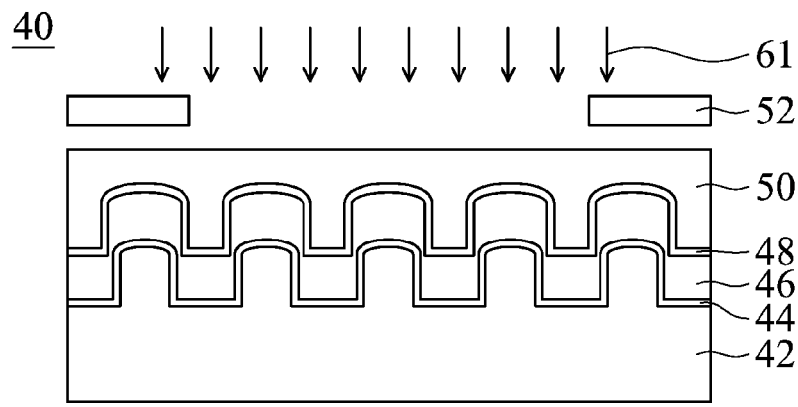
FIGS. 4A-4C show a series of cross-sectional schematic representations of a method for fabricating a surface-enhanced Raman scattering (SERS) substrate in accordance with an embodiment of the disclosure.
Figure 4B:
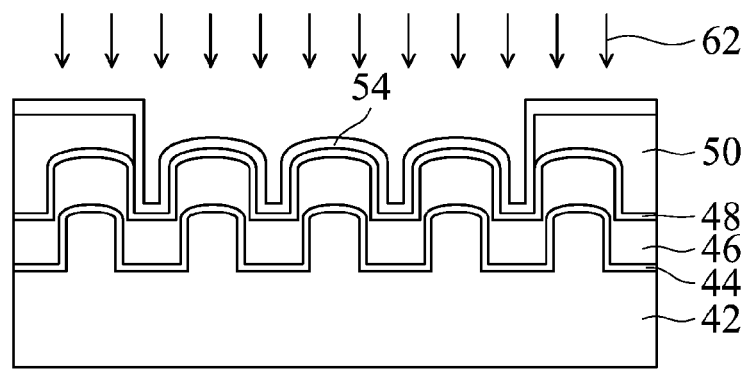
Figure 4C:
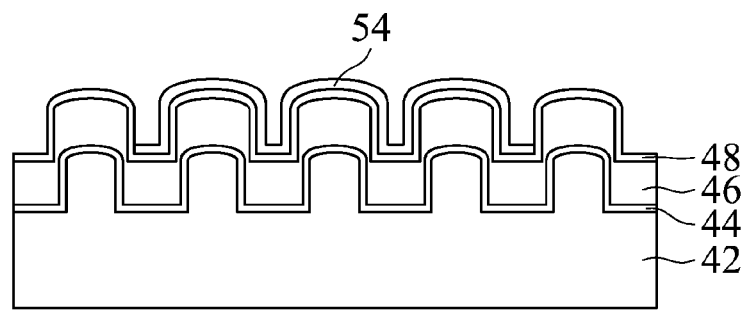

FIGS. 4A-4C show a series of cross-sectional schematic representations of a method for fabricating a surface-enhanced Raman scattering (SERS) substrate in accordance with an embodiment of the disclosure.

Referring to FIG. 4A, a reflection layer 44, a dielectric layer 46 and a metal thin layer 48 are sequentially formed on a substrate 42. The substrate 42 has periodic nano-structures, and an aspect ratio of the periodic nano-structures is about 0.1 to 3. A surface-enhanced Raman scattering (SERS) substrate is constructed by the substrate 42, the reflection layer 44, the dielectric layer 46 and the metal thin layer 48.

The reflection layer 44 is conformally formed on the substrate 42 having periodic nano-structures. The reflection layer 44 is used to shield the substrate 42 to avoid the self-absorption and the background signal of the substrate 42. Therefore, a thickness of the reflection layer 44 should be greater than a skin depth operated under a specific Laser wavelength.

The reflection layer 44 has a reflectivity greater than about 79%. In some embodiments, the reflection layer 44 has a reflectivity larger than about 85%. The reflection layer 44 is made of a material comprising metal, metal alloy, or dielectric layer. The metal comprises silver (Ag), aluminum (Al), gold (Au), copper (Cu), rhodium (Rh), or platinum (Pt). The metal alloy comprises copper-aluminum alloy or gold-nickel alloy. The dielectric layer comprises silicon (Si) or germanium (Ge).

The dielectric layer 46 is used to adjust the length of a Fabry-Perot resonator. In other words, the wavelength of the Fabry-Perot resonant mode is adjusted by the dielectric layer 46. The dielectric layer 46 is made of materials with a refractive index (n) in a range from 1.3 to 5.0, such as silicon dioxide (n=1.5), aluminum oxide (n=1.77), silicon nitride (n=2), titanium oxide (n=2.9), or silicon (n=4).

The metal thin layer 44 comprises gold (Au), silver (Ag), platinum (Pt), iron (Fe), cobalt (Co), nickel (Ni), copper (Cu), aluminum (Al), chromium (Cr), or an alloy thereof. The metal thin layer 44 is used to excite the surface plasma, and thus the Raman scattering signal is further improved. An embodiment is that silver as the metal thin layer 44 is coated on a nano-structure to form a hydrophobic surface.

Afterwards, a photoresist 50 is formed on a portion of the metal thin layer 48 by using a mask 52 by a lithography process 61. Therefore, a patterned photoresist is obtained.

Referring to FIG. 4B, a hydrophilic layer 54 is formed on the metal thin layer 48 by performing a plasma-assisted deposition process 62. During the plasma-assisted deposition process 62, a precursor is used. The precursor comprises polysiloxane, tetraethoxysilane (TEOS), tetramethoxysilane, hexamethyldisiloxane (HMDSO), HMDS, aluminum butoxide, diethylzinc, triethylaluminum, trimethylaluminum, metal alkyls, titanium tetraisopropoxide, titanium tetrapropoxide, metal alkoxides, metal nitrate, metal acetate, metal sulphate, metal chloride or combinations thereof.

Referring to FIG. 4C, the photoresist 50 is removed, a hydrophilic layer 54 is formed on a portion of the metal thin layer 48 (a portion of the metal thin film 48 is not covered by the hydrophilic layer 54). Therefore, a SERS substrate 40 with patterned hydrophilic region (the hydrophilic layer 54) and a patterned hydrophobic region (without a hydrophilic layer) is obtained.

It should be noted that because the substrate 42 has periodic nano-structures, the patterned hydrophobic region can be composed of these periodic hydrophobic nano-structures. In another embodiment, the patterned hydrophilic region can be composed of these periodic hydrophilic nano-structures.

Figure 5B:
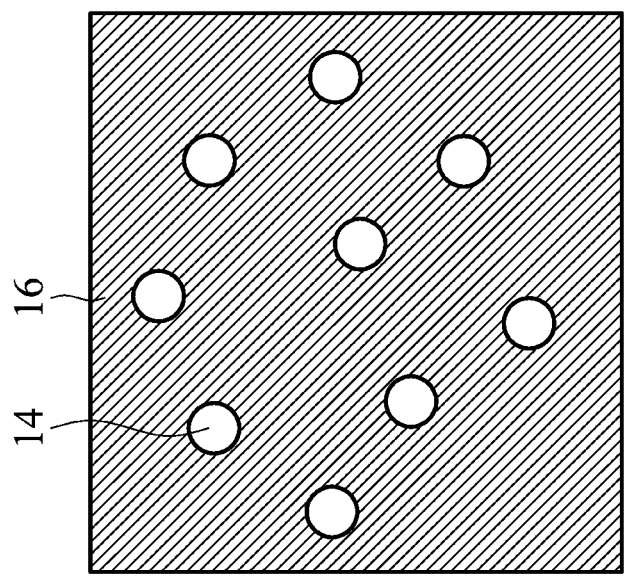
FIGS. 5A-5B show a series of cross-sectional schematic representations of a surface-enhanced Raman scattering (SERS) substrate with a plurality of patterned hydrophilic regions and a plurality of patterned hydrophobic regions in accordance with an embodiment of the disclosure.
Figure 5A:
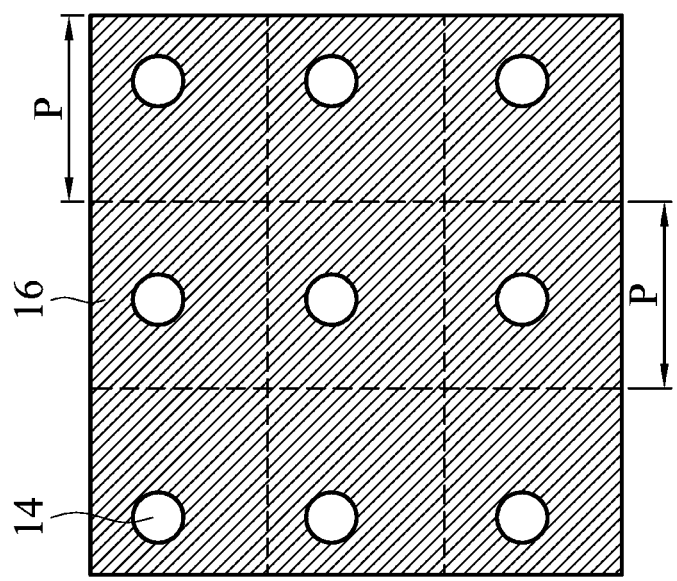

Referring to FIG. 5A-5B, the SERS substrate has a plurality of patterned hydrophilic regions 14 and a plurality of the patterned hydrophobic regions 16. Referring to FIG. 5A, the patterned hydrophilic regions 14 are arranged regularly, and they are surrounded by the patterned hydrophobic regions 16. A structure unit is constructed by the circular patterned hydrophilic regions 14 and the patterned hydrophobic regions 16. The structure unit has a unit length P in a range from 0.05 µm to 500 µm. It should be noted that each patterned hydrophilic region 14 in FIG. 5A is a hydrophilic layer with a thickness in a range from 0.01 nm to 10 nm, and each patterned hydrophobic region 16 is a SERS-active substrate 12 with a hydrophobic surface.

Referring to FIG. 5B, the patterned hydrophilic region 14 is arranged irregularly.

Compared with a comparative example without patterned hydrophilic regions and patterned hydrophobic regions, the analyte is distributed uniformly on the patterned hydrophilic regions or the patterned hydrophobic regions of the SERS substrate of the disclosure, and therefore the accuracy of the quantitative determination is improved. As a result, the Raman scattering signal is increased and the limit of detection (LOD) is decreased.

From the above description, a water contact angle difference between the patterned hydrophilic region and the patterned hydrophobic region is in a range from about 29 degrees to about 90 degrees. The analyte is distributed uniformly on specific regions and is concentrated. Therefore, Raman scattering signal is increased and limit of detection (LOD) is decreased.

EXAMPLE

Example 1 Fabricating a Surface-Enhanced Raman Scattering (SERS) Substrate

FIG. 4A-4C show a series of cross-sectional schematic representations of a method for fabricating the SERS substrate. Referring to FIG. 4A, 35 nm of gold layer 44, 100 nm of silicon dioxide as the dielectric layer 46, 15 nm of silver as the metal thin layer 46 were sequentially formed on a substrate 42. The top silver nano-structures had a hydrophobic surface. Afterwards, a lithography process was performed to form a patterned photoresist on a portion (hydrophobic surface) of the metal thin layer 48.

Referring to FIG. 4B, a hydrophilic layer 54 was formed on (hydrophobic) metal thin layer 48 by the plasma-assisted deposition process. During the plasma-assisted deposition process, tetraethoxysilane (TEOS) was used a precursor at room temperature under 1 atm. The hexamethyldisiloxane (HMDSO) was heated at 30° C. for six seconds to form a 10 nm of silicon dioxide over the metal thin layer 8.

Referring to FIG. 4C, the photoresist 50 is removed and a hydrophilic layer 54 was formed on a portion of the metal thin layer 48 (a portion of the metal thin layer 48 was not covered by the hydrophilic layer 54). Therefore, the SERS substrate 40 with the patterned hydrophilic region and the patterned hydrophobic region are obtained.

Table 1 shows a water contact angle of the patterned hydrophilic region and the patterned hydrophobic region.

| Example | Hydrophilic layer | water contact angle in the patterned hydrophilic region | water contact angle in the patterned hydrophobic region |
|---|---|---|---|
| Example 1 | Silicon dioxide | 120 degrees | 30 degrees |

The Raman Scattering Signal of the Analyte $10^{-3}$M-$10^{-5}$M of melamine solution was dripped on the SERS substrate of Example 1, and then the SERS substrate was dried at an environment at about 20° C., 50% of relative humidity for about 1 hour.

Afterwards, the analyte was measured. In order to compare with the distribution uniformity of analyte, the analyte was analyzed six times for each concentration at 685 cm$^{-1}$ wavelength, which was the characteristic Raman peak. The measured Raman scattering signal was averaged and calculated to obtain an average value and a standard derivation (STDEV) value.

Comparative Example 1 is a SERS substrate like FIG. 4A but without any patterned regions formed thereof.

Table 2 shows the SERS signal of Example 1. Table 3 shows the SERS signal of Comparative Example 1. Compared with Comparative Example 1, the analyte is distributed uniformly by the SERS substrate of Example 1, and the Raman scattering signal intensity is improved (higher than 3 folds).

Figure 6:
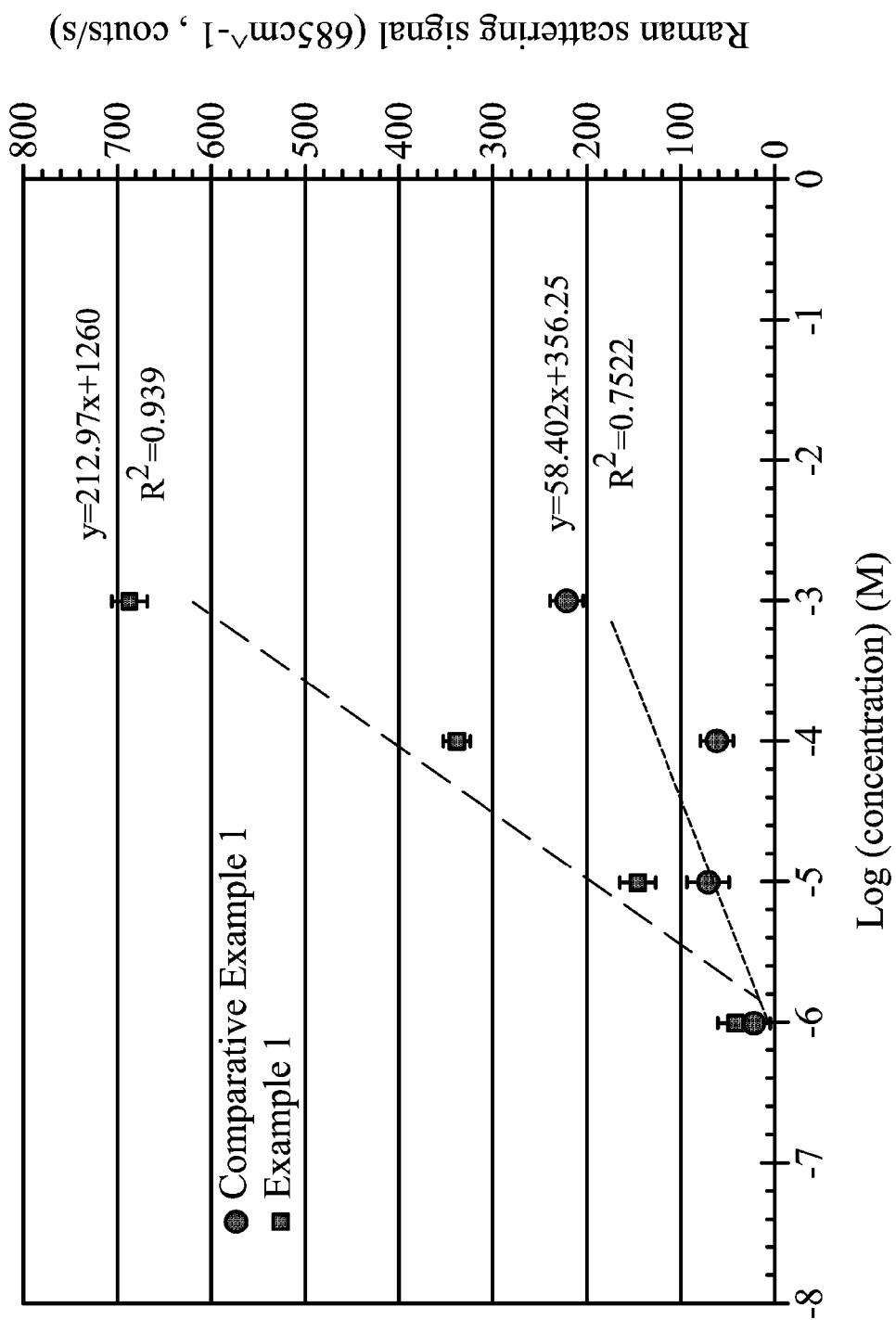
FIG. 6 shows a concentration VS. Raman scattering signal relationship between the Example 1 and Comparative Example 1 in accordance with an embodiment of the disclosure.

FIG. 6 shows a concentration VS. Raman scattering signal relationship between Example 1 and Comparative Example 1. As shown in FIG. 6, the limit of detection (LOD) of analyte improved from 0.72 ppm (Comparative Example 1) to 0.25 ppm (Example 1). The concentration linearity ($R^2$) also improved from 0.752 (Comparative Example 1) to 0.939 (Example 1).

TABLE 2

Example 1

|  | $10^{-3}$ M melamine | $10^{-4}$ M melamine | $10^5$ M melamine |
|---|---|---|---|
| average | 684.7 | 337.4 | 145.4 |
| Standard derivation(STDEV) | 5.47% | 6.61% | 26.44% |

TABLE 3

Comparative Example 1

|  | $10^{-3}$ M melamine | $10^{-4}$ M melamine | $10^{-5}$ M melamine |
|---|---|---|---|
| average | 220.0 | 61.1 | 70.4 |
| Standard derivation(STDEV) | 10.8% | 45.9% | 67.8% |

Examples 4-10

Examples 4-10 are similar to Example 1, the difference is that a different hydrophilic layer is formed.

Table 4 shows the different hydrophilic layer and corresponding water contact angle. As shown in Table 4, when the water contact angle difference between the patterned hydrophilic region and the patterned hydrophobic region is in a range from about 29 degrees to about 90 degrees, the analyte is limited to the boundary of the patterned hydrophilic or hydrophobic region. As shown in FIG. 4, the effect description marked as "OK" represents the analyte being confined on a boundary of the patterned hydrophilic or the hydrophobic region. The effect description marked as "NG" represents the analyte being not confined on a boundary of patterned hydrophilic or hydrophobic region, and therefore the analyte diffuses.

TABLE 4

| Example | Hydrophilic layer | water contact angle in the patterned hydrophilic region (degrees) | water contact angle in the patterned hydrophobic region (degrees) | Difference of water contact angle (degrees) | Effect description |
|---|---|---|---|---|---|
| 1 | SiOx | 30 | 120 | 90 | OK |
| 4 | Polysiloxane | 23.47 | 102 | 78.54 | OK |
| 5 | Polysiloxane | 28.47 | 103.18 | 74.72 | OK |
| 6 | Polysiloxane | 32.35 | 99.4 | 67.05 | OK |
| 7 | Polysiloxane | 49.24 | 105.68 | 56.44 | OK |
| 8 | Polysiloxane | 72.61 | 102.1 | 29.49 | OK |
| 9 | Polysiloxane | 95.28 | 103.46 | 8.18 | NG |
| 10 | Polysiloxane | 107.3 | 105.99 | −1.31 | NG |

While the disclosure has been described by way of example and in terms of the preferred embodiments, it is to be understood that the disclosure is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A surface-enhanced Raman scattering substrate, comprising:
    a surface-enhanced Raman scattering (SERS)-active substrate, wherein the SERS-active substrate is composed of nano-structures; and
    a patterned hydrophilic region and a patterned hydrophobic region formed on the SERS-active substrate, wherein a water contact angle difference between the patterned hydrophilic region and the patterned hydrophobic region is in a range from about 29 degrees to about 90 degrees.

2. The surface-enhanced Raman scattering substrate as claimed in claim 1, wherein the patterned hydrophilic region is made of a material comprising an organic material or inorganic material.

3. The surface-enhanced Raman scattering substrate as claimed in claim 2, wherein the organic material comprises polysiloxane, tetraethoxysilane (TEOS), tetramethoxysilane, hexamethyldisiloxane (HMDS), HMDS, aluminum butoxide, diethylzinc, triethylaluminum, trimethylaluminum, metal alkyls, titanium tetraisopropoxide, titanium tetrapropoxide, metal alkoxides, zinc nitrate, aluminum nitrate, metal nitride, zinc acetate, aluminum acetate, tin acetate, metal acetate, zinc sulfate, aluminum sulfate, stannous sulfate, metal sulfate, zinc chloride, zirconium tetrachloride, aluminum chloride, titanium chloride, metal chloride, metal chloride liquid, metal chloride steam or vapor, or combinations thereof.

4. The surface-enhanced Raman scattering substrate as claimed in claim 2, wherein the inorganic material comprises silicon oxide (SiO2), metal, metal oxide or combinations thereof.

5. The surface-enhanced Raman scattering substrate as claimed in claim 4, wherein the metal comprises silver (Ag), gold (Au), zinc (Zn), zirconium (Zr), tin (Sn), titanium (Ti), barium (Ba), platinum (Pt), aluminum (Al) or combinations thereof.

6. The surface-enhanced Raman scattering substrate as claimed in claim 1, wherein the patterned hydrophobic region is made of a material comprising polytetrafluoroethene, 1H,1H,2H,2H-Perfluorooctyltrichlorosilane or combinations thereof.

7. The surface-enhanced Raman scattering substrate as claimed in claim 1, wherein the patterned hydrophilic region and the patterned hydrophobic region independently comprises a regular or irregular shape.

8. The surface-enhanced Raman scattering substrate as claimed in claim 7, wherein the regular shape comprises a circular, rectangular or triangle shape.

9. The surface-enhanced Raman scattering substrate as claimed in claim 7, wherein when the patterned hydrophilic region or the patterned hydrophobic region has a regular shape, a unit length of the patterned hydrophilic region or the patterned hydrophobic region is in a range from 0.05 μm to about 500 μm.

10. The surface-enhanced Raman scattering substrate as claimed in claim 1, wherein a ratio of an area of the patterned hydrophobic region to an area of the patterned hydrophilic region is in a range from 0.1 to 0.9.

11. The surface-enhanced Raman scattering substrate as claimed in claim 1, wherein when the patterned hydrophilic region is a hydrophilic layer, the patterned hydrophobic region is the SERS-active substrate with a hydrophobic surface.

12. The surface-enhanced Raman scattering substrate as claimed in claim 11, wherein when an analyte is disposed on the hydrophilic layer, the hydrophilic layer has a thickness in a range from about 0.01 nm to about 10 nm.

13. The surface-enhanced Raman scattering substrate as claimed in claim 1, wherein when the patterned hydrophobic region is a hydrophobic layer, the patterned hydrophilic region is the SERS-active substrate with a hydrophilic surface.

14. The surface-enhanced Raman scattering substrate as claimed in claim 13, wherein when an analyte is disposed on the hydrophobic layer, the hydrophobic layer has a thickness in a range from about 0.01 nm to about 10 nm.

15. The surface-enhanced Raman scattering substrate as claimed in claim 1, wherein the patterned hydrophilic region is a hydrophilic layer, and the patterned hydrophobic region is a hydrophobic layer.

16. The surface-enhanced Raman scattering substrate as claimed in claim 1, wherein the patterned hydrophilic region or the patterned hydrophobic region is arranged regularly or irregularly.

17. The surface-enhanced Raman scattering substrate as claimed in claim 1, wherein the patterned hydrophilic region is a hydrophilic surface with nano-structures.

18. The surface-enhanced Raman scattering substrate as claimed in claim 1, wherein the patterned hydrophobic region is a hydrophobic surface with nano-structures.

* * * * *